United States Patent [19]

Bushell et al.

[11] Patent Number: 4,937,388
[45] Date of Patent: Jun. 26, 1990

[54] INSECTICIDAL ETHERS

[75] Inventors: Michael J. Bushell, Wokingham; Robin A. E. Carr, Camberley, both of England

[73] Assignee: Imperial Chemical Industries PLC, London, England

[21] Appl. No.: 114,038

[22] Filed: Oct. 29, 1987

[30] Foreign Application Priority Data

Aug. 9, 1986 [GB] United Kingdom ............... 8520027
Oct. 29, 1986 [GB] United Kingdom ............... 8625897

[51] Int. Cl.$^5$ ..................... C07C 148/00; C07C 67/02
[52] U.S. Cl. ........................................ 568/56; 568/38; 568/39; 568/31; 568/28; 568/37; 568/27; 549/15; 560/254; 514/548
[58] Field of Search ................. 568/38, 39, 31, 37, 568/28, 56, 27; 560/254; 549/15; 574/548

[56] References Cited

U.S. PATENT DOCUMENTS 4,678,811  7/1987  Franke et al. ..................... 514/721

FOREIGN PATENT DOCUMENTS 0104908  4/1984  European Pat. Off. .
240978  10/1987  European Pat. Off. .

Primary Examiner—Paul J. Killos
Attorney, Agent, or Firm—Cushman, Darby & Cushman

[57] ABSTRACT

The invention provides insecticidally active compounds of formula I:

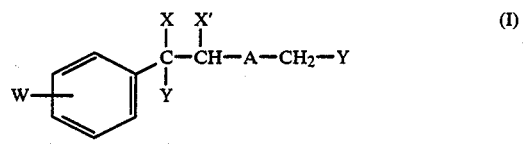

wherein A is selected from oxygen and a group of formula $S(O)_n$, where n represents 0, 1 or 2; W represents one or two substituents selected from halo, alkyl, alkoxy, alkoxyalkyl, haloalkyl and haloalkoxy, or W represents a bidentate group linking adjacent carbon atoms, selected from alkylene and alkylenedioxy; Y represents a substituted aryl group where each substituent is selected from halo, alkyl, aryl, aralkyl, aryloxy and arylamino; Z represents a fluoroalkyl group of up to two carbon atoms; and either X' represents hydrogen and X is selected from hydrogen, halo, hydroxy, alkoxy and acyloxy, or X and X' together represent a second bond between the adjacent carbon atoms.

The invention also provides processes and intermediates useful for the preparation of the compounds of formula I, insecticidal compositions comprising the compounds of formula I, and methods of combating and controlling pests therewith.

11 Claims, No Drawings

INSECTICIDAL ETHERS

This Application is a continuation-in-part of copending application Ser. No. 891,350, filed 31 July 1986, the disclosure of which is herein incorporated by reference.

This invention relates to novel insecticidally active compounds, to processes and intermediates for their preparation, to insecticidal compositions thereof, and to methods of combating and controlling pests therewith.

In a first aspect the invention provides compounds of formula I:

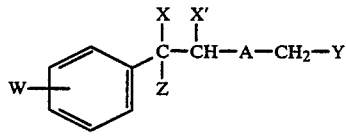

wherein A is selected from oxygen and a group of formula $S(O)_n$, where n represents 0, 1 or 2; W represents one or two substituents selected from halo, alkyl, alkoxy, alkoxyalkyl, haloalkyl and haloalkoxy, or W represents a bidentate group linking adjacent carbon atoms, selected from alkylene and alkylenedioxy; Y represents a substituted aryl group where each substituent is selected from halo, alkyl, aryl, aralkyl, aryloxy and arylamino; Z represents a fluoroalkyl group of up to two carbon atoms; and either X' in hydrogen and X is selected from hydrogen, hydroxy, halo alkoxy and acyloxy, or X and X' together represent a second bond between the adjacent carbon atoms.

Preferred compounds according to the invention are those according to formula IA:

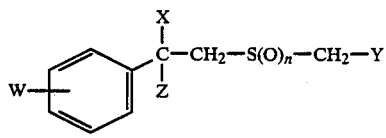

wherein W represents one or two substituents selected from halo, alkyl of up to six carbon atoms, alkoxy of up to six carbon atoms, alkoxyalkyl of up to a total of six carbon atoms, haloalkyl of up to six carbon atoms, and haloalkoxy of up to six carbon atoms, or W represents a bidentate group linking adjacent carbon atoms selected from alkylene of up to six carbon atoms and alkylenedioxy of up to a total of six carbon atoms; X is selected from hydrogen, halo, hydroxy, alkoxy of up to six carbon atoms and acyloxy of up to six carbon atoms; Y respresents an aryl group selected from phenyl, pyridyl and furyl, substituted with one or more substituents selected from fluoro, methyl, phenyl, benzyl, phenoxy, chlorophenoxy, fluorophenoxy, bromophenoxy and fluoroanilino; Z represents a fluoroalkyl group of one or two carbon atoms; and n may have a value selected from 0, 1 and 2.

Particularly preferred compounds of formula IA are those wherein Z represents the trifluoromethyl group; W represents a substituent in the 4-position selected from chloro, methoxy, ethoxy, trifluoromethyl, trifluoromethoxy, andd difluoromethoxy; Y represents a phenoxyphenyl or a phenoxypyridyl group in which the phenyl or pyridyl rings may be unsubstituted or substituted with halogen; X is selected from hydrogen, fluoro and chloro; and n has the value 0.

Particular examples of compounds according to the invention include those set out in Table I. In Table I, Y is defined as $R^1$ to $R^{14}$ wherein $R^1$ to $R^{14}$ represent the following groups:

$R^1$: 3-phenoxyphenyl
$R^2$: 3-(4-chlorophenoxy)phenyl
$R^3$: 4-fluoro-3-phenoxyphenyl     $R^4$: 3-(4-bromophenoxy)phenyl
$R^5$: 4-fluoro-3-(4-bromophenoxy)phenyl
$R^6$: 4-fluoro-3-(4-chlorophenoxy)phenyl
$R^7$: 3-(2,4-difluorophenoxy)phenyl
$R^8$: 3-benzylphenyl
$R^9$: 3-benzyl-4-fluorophenyl
$R^{10}$: 3-(4-fluorophenylamino)phenyl
$R^{11}$: 6-phenoxypyrid-2-yl
$R^{12}$: 2-methyl-3-phenylphenyl
$R^{13}$: 4-methyl-2,3,5,6-tetrafluorophenyl
$R^{14}$: 5-benzylfuran-3-yl

TABLE I

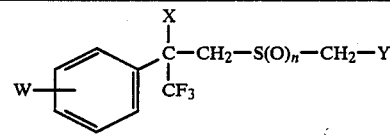

| COMPOUND NO. | W | X | Y | n |
|---|---|---|---|---|
| 1 | 4-OC$_2$H$_5$ | H | $R^1$ | 0 |
| 2 | 4-OC$_2$H$_5$ | H | $R^{13}$ | 0 |
| 3 | 4-OC$_2$H$_5$ | H | $R^2$ | 0 |
| 4 | 4-OC$_2$H$_5$ | H | $R^{11}$ | 0 |
| 5 | 4-OC$_2$H$_5$ | H | $R^6$ | 0 |
| 6 | 4-OC$_2$H$_5$ | H | $R^5$ | 0 |
| 7 | 4-OC$_2$H$_5$ | H | $R^{12}$ | 0 |
| 8 | 4-OC$_2$H$_5$ | H | $R^9$ | 0 |
| 9 | 4-OC$_2$H$_5$ | H | $R^4$ | 0 |
| 10 | 4-OC$_2$H$_5$ | H | $R^7$ | 0 |
| 11 | 4-OC$_2$H$_5$ | H | $R^{10}$ | 0 |
| 12 | 4-OC$_2$H$_5$ | H | $R^8$ | 0 |
| 13 | 3-F,4-OC$_2$H$_5$ | H | $R^2$ | 0 |
| 14 | 3-F,4-OC$_2$H$_5$ | H | $R^1$ | 0 |
| 15 | 4-Cl | H | $R^3$ | 0 |
| 16 | 4-Cl | H | $R^1$ | 0 |
| 17 | 2,4-Cl$_2$ | H | $R^1$ | 0 |
| 18 | 4-F | H | $R^3$ | 0 |
| 19 | 3,4-(CH$_2$)$_3$ | H | $R^3$ | 0 |
| 20 | 4-(CH$_2$)$_2$CH$_3$ | H | $R^3$ | 0 |
| 21 | 4-C(CH$_3$)$_3$ | H | $R^3$ | 0 |
| 22 | 4-CH$_3$ | H | $R^1$ | 0 |
| 23 | 4-CH$_2$OCH$_3$ | H | $R^2$ | 0 |
| 24 | 4-CH$_2$OCH$_3$ | H | $R^1$ | 0 |
| 25 | 4-OCF$_3$ | H | $R^3$ | 0 |
| 26 | 4-OCF$_3$ | H | $R^2$ | 0 |
| 27 | 4-OCF$_3$ | H | $R^1$ | 0 |
| 28 | 4-OCF$_3$ | H | $R^{11}$ | 0 |
| 29 | 4-OCH$_3$ | H | $R^3$ | 0 |
| 30 | 4-OCH$_3$ | H | $R^1$ | 0 |
| 31 | 3,4-(OCH$_2$O) | H | $R^1$ | 0 |
| 32 | 3,4-(OCH$_2$O) | H | $R^2$ | 0 |
| 33 | 4-OC$_2$H$_5$ | H | $R^3$ | 0 |
| 34 | 4-CF$_3$ | H | $R^1$ | 0 |
| 35 | 4-Br | H | $R^3$ | 0 |
| 36 | 4-CF$_3$ | H | $R^3$ | 0 |
| 37 | 4-OC$_2$H$_5$ | H | $R^{14}$ | 0 |
| 38 | 4-OC$_2$H$_5$ | Cl | $R^1$ | 0 |
| 39 | 4-OC$_2$H$_5$ | Cl | $R^{13}$ | 0 |
| 40 | 4-OC$_2$H$_5$ | Cl | $R^3$ | 0 |
| 41 | 4-OC$_2$H$_5$ | Cl | $R^{11}$ | 0 |
| 42 | 4-OC$_2$H$_5$ | Cl | $R^2$ | 0 |
| 43 | 4-OC$_2$H$_5$ | Cl | $R^5$ | 0 |
| 44 | 4-OC$_2$H$_5$ | Cl | $R^6$ | 0 |
| 45 | 4-OC$_2$H$_5$ | Cl | $R^{14}$ | 0 |
| 46 | 4-OC$_2$H$_5$ | Cl | $R^{12}$ | 0 |
| 47 | 4-OC$_2$H$_5$ | Cl | $R^9$ | 0 |
| 48 | 3-F,4-OC$_2$H$_5$ | Cl | $R^2$ | 0 |
| 49 | 3-F,4-OC$_2$H$_5$ | Cl | $R^1$ | 0 |
| 50 | 4-Cl | Cl | $R^3$ | 0 |

TABLE I-continued

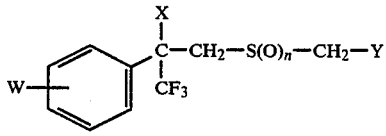

| COMPOUND NO. | W | X | Y | n |
|---|---|---|---|---|
| 51 | 4-F | Cl | R³ | 0 |
| 52 | 3,4-(CH₂)₃ | Cl | R³ | 0 |
| 53 | 4-(CH₂)₂CH₃ | Cl | R³ | 0 |
| 54 | 4-C(CH₃)₃ | Cl | R³ | 0 |
| 55 | 4-CH₃ | Cl | R¹ | 0 |
| 56 | 4-CH₂OCH₃ | Cl | R² | 0 |
| 57 | 4-CH₂OCH₃ | Cl | R¹ | 0 |
| 58 | 4-OCF₃ | Cl | R³ | 0 |
| 59 | 4-OCF₃ | Cl | R¹ | 0 |
| 60 | 4-OCF₃ | Cl | R² | 0 |
| 61 | 4-OCF₃ | Cl | R¹¹ | 0 |
| 62 | 4-OCH₃ | Cl | R³ | 0 |
| 63 | 4-OCH₃ | Cl | R¹ | 0 |
| 64 | 3,4-(OCH₂O) | Cl | R¹ | 0 |
| 65 | 3,4-(OCH₂O) | Cl | R² | 0 |
| 66 | 4-Cl | Cl | R¹ | 0 |
| 67 | 2,4-Cl₂ | Cl | R¹ | 0 |
| 68 | 4-CF₃ | Cl | R¹ | 0 |
| 69 | 4-Br | Cl | R³ | 0 |
| 70 | 4-CF₃ | Cl | R³ | 0 |
| 71 | 4-OC₂H₅ | Cl | R⁴ | 0 |
| 72 | 4-OC₂H₅ | Cl | R⁷ | 0 |
| 73 | 4-OC₂H₅ | Cl | R⁸ | 0 |
| 74 | 4-OC₂H₅ | Cl | R¹⁰ | 0 |
| 75 | 4-OC₂H₅ | F | R¹ | 0 |
| 76 | 4-OC₂H₅ | F | R¹¹ | 0 |
| 77 | 4-OC₂H₅ | F | R³ | 0 |
| 78 | 4-OC₂H₅ | F | R¹³ | 0 |
| 79 | 4-OC₂H₅ | F | R² | 0 |
| 80 | 4-OC₂H₅ | F | R¹² | 0 |
| 81 | 4-Cl | F | R³ | 0 |
| 82 | 4-OCF₃ | F | R¹ | 0 |
| 83 | 4-Br | F | R³ | 0 |
| 84 | 4-CF₃ | F | R¹ | 0 |
| 85 | 4-Cl | F | R¹ | 0 |
| 86 | 2,4-Cl₂ | F | R¹ | 0 |
| 87 | 4-CH₃ | F | R¹ | 0 |
| 88 | 4-OCH₃ | F | R¹ | 0 |
| 89 | 3-F,4-OC₂H₅ | F | R¹ | 0 |
| 90 | 3,4-(OCH₂O) | F | R¹ | 0 |
| 91 | 4-CH₂OCH₃ | F | R¹ | 0 |
| 92 | 3-F,4-OC₂H₅ | F | R² | 0 |
| 93 | 3,4-(OCH₂O) | F | R² | 0 |
| 94 | 4-OCF₃ | F | R² | 0 |
| 95 | 4-CH₂OCH₃ | F | R² | 0 |
| 96 | 4-F | F | R³ | 0 |
| 97 | 4-C(CH₃)₃ | F | R³ | 0 |
| 98 | 4-OCH₃ | F | R³ | 0 |
| 99 | 4-(CH₂)₂CH₃ | F | R³ | 0 |
| 100 | 3,4-(CH₂)₃ | F | R³ | 0 |
| 101 | 4-OCF₃ | F | R³ | 0 |
| 102 | 4-CF₃ | F | R³ | 0 |
| 103 | 4-OC₂H₅ | F | R⁴ | 0 |
| 104 | 4-OC₂H₅ | F | R⁵ | 0 |
| 105 | 4-OC₂H₅ | F | R⁶ | 0 |
| 106 | 4-OC₂H₅ | F | R⁷ | 0 |
| 107 | 4-OC₂H₅ | F | R⁸ | 0 |
| 108 | 4-OC₂H₅ | F | R⁹ | 0 |
| 109 | 4-OC₂H₅ | F | R¹⁰ | 0 |
| 110 | 4-OCF₃ | F | R¹¹ | 0 |
| 111 | 4-OC₂H₅ | F | R¹⁴ | 0 |
| 112 | 4-OC₂H₅ | OH | R¹ | 0 |
| 113 | 4-OC₂H₅ | OH | R³ | 0 |
| 114 | 4-OC₂H₅ | OH | R¹³ | 0 |
| 115 | 4-OC₂H₅ | OH | R² | 0 |
| 116 | 4-OC₂H₅ | OH | R⁵ | 0 |
| 117 | 4-OC₂H₅ | OH | R⁶ | 0 |
| 118 | 4-OC₂H₅ | OH | R¹⁴ | 0 |
| 119 | 4-OC₂H₅ | OH | R⁹ | 0 |
| 120 | 4-CH₃ | OH | R¹ | 0 |
| 121 | 3-F,4-OC₂H₅ | OH | R² | 0 |
| 122 | 4-C(CH₃)₃ | OH | R³ | 0 |

TABLE I-continued

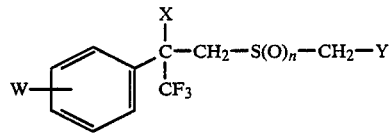

| COMPOUND NO. | W | X | Y | n |
|---|---|---|---|---|
| 123 | 4-(CH₂)₂CH₃ | OH | R³ | 0 |
| 124 | 3,4-(CH₂)₃ | OH | R³ | 0 |
| 125 | 4-F | OH | R³ | 0 |
| 126 | 4-Cl | OH | R³ | 0 |
| 127 | 4-Br | OH | R³ | 0 |
| 128 | 3,4-(OCH₂O) | OH | R¹ | 0 |
| 129 | 3,4-(OCH₂O) | OH | R² | 0 |
| 130 | 4-OCH₃ | OH | R¹ | 0 |
| 131 | 4-OCH₃ | OH | R³ | 0 |
| 132 | 4-CH₂OCH₃ | OH | R² | 0 |
| 133 | 4-CH₂OCH₃ | OH | R¹ | 0 |
| 134 | 4-OCF₃ | OH | R³ | 0 |
| 135 | 4-OCF₃ | OH | R² | 0 |
| 136 | 4-OCF₃ | OH | R¹¹ | 0 |
| 137 | 4-CF₃ | OH | R¹ | 0 |
| 138 | 4-CF₃ | OH | R³ | 0 |
| 139 | 4-OCF₃ | OH | R¹ | 0 |
| 140 | 3-F,4-OC₂H₅ | OH | R¹ | 0 |
| 141 | 4-OC₂H₅ | OH | R¹¹ | 0 |
| 142 | 4-OC₂H₅ | OH | R¹² | 0 |
| 143 | 4-Cl | OH | R¹ | 0 |
| 144 | 2,4-Cl₂ | OH | R² | 0 |
| 145 | 4-OC₂H₅ | OH | R⁴ | 0 |
| 146 | 4-OC₂H₅ | OH | R⁷ | 0 |
| 147 | 4-OC₂H₅ | OH | R⁸ | 0 |
| 148 | 4-OC₂H₅ | OH | R¹⁰ | 0 |
| 149 | 4-OC₂H₅ | OCOCH₃ | R³ | 0 |
| 150 | 4-OC₂H₅ | OCH₃ | R³ | 0 |
| 151 | 4-OCHF₂ | H | R¹ | 0 |
| 152 | 4-OCHF₂ | H | R² | 0 |
| 153 | 4-OCHF₂ | H | R³ | 0 |
| 154 | 4-OCHF₂ | Cl | R¹ | 0 |
| 155 | 4-OCHF₂ | Cl | R² | 0 |
| 156 | 4-OCHF₂ | Cl | R³ | 0 |
| 157 | 4-OCHF₂ | F | R¹ | 0 |
| 158 | 4-OCHF₂ | F | R² | 0 |
| 159 | 4-OCHF₂ | F | R³ | 0 |
| 160 | 4-OCHF₂ | OH | R¹ | 0 |
| 161 | 4-OCHF₂ | OH | R² | 0 |
| 162 | 4-OCHF₂ | OH | R³ | 0 |
| 163 | 4-OC₂H₅ | H | R¹ | 1 |
| 164 | 4-OC₂H₅ | H | R¹³ | 1 |
| 165 | 4-OC₂H₅ | H | R² | 1 |
| 166 | 4-OC₂H₅ | H | R¹¹ | 1 |
| 167 | 4-OC₂H₅ | H | R⁶ | 1 |
| 168 | 4-OC₂H₅ | H | R⁵ | 1 |
| 169 | 4-OC₂H₅ | H | R¹² | 1 |
| 170 | 4-OC₂H₅ | H | R⁹ | 1 |
| 171 | 4-OC₂H₅ | H | R⁴ | 1 |
| 172 | 4-OC₂H₅ | H | R⁷ | 1 |
| 173 | 4-OC₂H₅ | H | R¹⁰ | 1 |
| 174 | 4-OC₂H₅ | H | R⁸ | 1 |
| 175 | 3-F,4-OC₂H₅ | H | R² | 1 |
| 176 | 3-F,4-OC₂H₅ | H | R¹ | 1 |
| 177 | 4-Cl | H | R³ | 1 |
| 178 | 4-Cl | H | R¹ | 1 |
| 179 | 2,4-Cl₂ | H | R¹ | 1 |
| 180 | 4-F | H | R³ | 1 |
| 181 | 3,4-(CH₂)₃ | H | R³ | 1 |
| 182 | 4-(CH₂)₂CH₃ | H | R³ | 1 |
| 183 | 4-C(CH₃)₃ | H | R³ | 1 |
| 184 | 4-CH₃ | H | R¹ | 1 |
| 185 | 4-CH₂OCH₃ | H | R² | 1 |
| 186 | 4-CH₂OCH₃ | H | R¹ | 1 |
| 187 | 4-OCF₃ | H | R³ | 1 |
| 188 | 4-OCF₃ | H | R² | 1 |
| 189 | 4-OCF₃ | H | R¹ | 1 |
| 190 | 4-OCF₃ | H | R¹¹ | 1 |
| 191 | 4-OCH₃ | H | R³ | 1 |
| 192 | 4-OCH₃ | H | R¹ | 1 |
| 193 | 3,4-(OCH₂O) | H | R¹ | 1 |
| 194 | 3,4-(OCH₂O) | H | R² | 1 |

TABLE I-continued

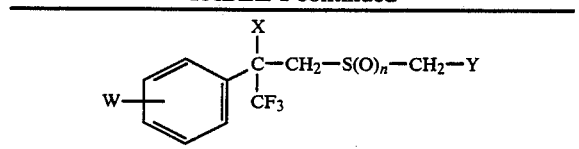

| COMPOUND NO. | W | X | Y | n |
|---|---|---|---|---|
| 195 | 4-OC$_2$H$_5$ | H | R$^3$ | 1 |
| 196 | 4-CF$_3$ | H | R$^1$ | 1 |
| 197 | 4-Br | H | R$^3$ | 1 |
| 198 | 4-CF$_3$ | H | R$^3$ | 1 |
| 199 | 4-OC$_2$H$_5$ | H | R$^{14}$ | 1 |
| 200 | 4-OC$_2$H$_5$ | Cl | R$^1$ | 1 |
| 201 | 4-OC$_2$H$_5$ | Cl | R$^{13}$ | 1 |
| 202 | 4-OC$_2$H$_5$ | Cl | R$^3$ | 1 |
| 203 | 4-OC$_2$H$_5$ | Cl | R$^{11}$ | 1 |
| 204 | 4-OC$_2$H$_5$ | Cl | R$^2$ | 1 |
| 205 | 4-OC$_2$H$_5$ | Cl | R$^5$ | 1 |
| 206 | 4-OC$_2$H$_5$ | Cl | R$^6$ | 1 |
| 207 | 4-OC$_2$H$_5$ | Cl | R$^{14}$ | 1 |
| 208 | 4-OC$_2$H$_5$ | Cl | R$^{12}$ | 1 |
| 209 | 4-OC$_2$H$_5$ | Cl | R$^9$ | 1 |
| 210 | 3-F,4-OC$_2$H$_5$ | Cl | R$^2$ | 1 |
| 211 | 3-F,4-OC$_2$H$_5$ | Cl | R$^1$ | 1 |
| 212 | 4-Cl | Cl | R$^3$ | 1 |
| 213 | 4-F | Cl | R$^3$ | 1 |
| 214 | 3,4-(CH$_2$)$_3$ | Cl | R$^3$ | 1 |
| 215 | 4-(CH$_2$)$_2$CH$_3$ | Cl | R$^3$ | 1 |
| 216 | 4-C(CH$_3$)$_3$ | Cl | R$^3$ | 1 |
| 217 | 4-CH$_3$ | Cl | R$^1$ | 1 |
| 218 | 4-CH$_2$OCH$_3$ | Cl | R$^2$ | 1 |
| 219 | 4-CH$_2$OCH$_3$ | Cl | R$^1$ | 1 |
| 220 | 4-OCF$_3$ | Cl | R$^3$ | 1 |
| 221 | 4-OCF$_3$ | Cl | R$^1$ | 1 |
| 222 | 4-OCF$_3$ | Cl | R$^2$ | 1 |
| 223 | 4-OCF$_3$ | Cl | R$^{11}$ | 1 |
| 224 | 4-OCH$_3$ | Cl | R$^3$ | 1 |
| 225 | 4-OCH$_3$ | Cl | R$^1$ | 1 |
| 226 | 3,4-(OCH$_2$O) | Cl | R$^1$ | 1 |
| 227 | 3,4-(OCH$_2$O) | Cl | R$^2$ | 1 |
| 228 | 4-Cl | Cl | R$^1$ | 1 |
| 229 | 2,4-Cl$_2$ | Cl | R$^1$ | 1 |
| 230 | 4-CF$_3$ | Cl | R$^1$ | 1 |
| 231 | 4-Br | Cl | R$^3$ | 1 |
| 232 | 4-CF$_3$ | Cl | R$^3$ | 1 |
| 233 | 4-OC$_2$H$_5$ | Cl | R$^4$ | 1 |
| 234 | 4-OC$_2$H$_5$ | Cl | R$^7$ | 1 |
| 235 | 4-OC$_2$H$_5$ | Cl | R$^8$ | 1 |
| 236 | 4-OC$_2$H$_5$ | Cl | R$^{10}$ | 1 |
| 237 | 4-OC$_2$H$_5$ | F | R$^1$ | 1 |
| 238 | 4-OC$_2$H$_5$ | F | R$^{11}$ | 1 |
| 239 | 4-OC$_2$H$_5$ | F | R$^3$ | 1 |
| 240 | 4-OC$_2$H$_5$ | F | R$^{13}$ | 1 |
| 241 | 4-OC$_2$H$_5$ | F | R$^2$ | 1 |
| 242 | 4-OC$_2$H$_5$ | F | R$^{12}$ | 1 |
| 243 | 4-Cl | F | R$^3$ | 1 |
| 244 | 4-OCF$_3$ | F | R$^1$ | 1 |
| 245 | 4-Br | F | R$^3$ | 1 |
| 246 | 4-CF$_3$ | F | R$^1$ | 1 |
| 247 | 4-Cl | F | R$^1$ | 1 |
| 248 | 2,4-Cl$_2$ | F | R$^1$ | 1 |
| 249 | 4-CH$_3$ | F | R$^1$ | 1 |
| 250 | 4-OCH$_3$ | F | R$^1$ | 1 |
| 251 | 3-F,4-OC$_2$H$_5$ | F | R$^1$ | 1 |
| 252 | 3,4-(OCH$_2$O) | F | R$^1$ | 1 |
| 253 | 4-CH$_2$OCH$_3$ | F | R$^1$ | 1 |
| 254 | 3-F,4-OC$_2$H$_5$ | F | R$^2$ | 1 |
| 255 | 3,4-(OCH$_2$O) | F | R$^2$ | 1 |
| 256 | 4-OCF$_3$ | F | R$^2$ | 1 |
| 257 | 4-CH$_2$OCH$_3$ | F | R$^2$ | 1 |
| 258 | 4-F | F | R$^3$ | 1 |
| 259 | 4-C(CH$_3$)$_3$ | F | R$^3$ | 1 |
| 260 | 4-OCH$_3$ | F | R$^3$ | 1 |
| 261 | 4-(CH$_2$)$_2$CH$_3$ | F | R$^3$ | 1 |
| 262 | 3,4-(CH$_2$)$_3$ | F | R$^3$ | 1 |
| 263 | 4-OCF$_3$ | F | R$^3$ | 1 |
| 264 | 4-CF$_3$ | F | R$^3$ | 1 |
| 265 | 4-OC$_2$H$_5$ | F | R$^4$ | 1 |
| 266 | 4-OC$_2$H$_5$ | F | R$^5$ | 1 |
| 267 | 4-OC$_2$H$_5$ | F | R$^6$ | 1 |
| 268 | 4-OC$_2$H$_5$ | F | R$^7$ | 1 |
| 269 | 4-OC$_2$H$_5$ | F | R$^8$ | 1 |
| 270 | 4-OC$_2$H$_5$ | F | R$^9$ | 1 |
| 271 | 4-OC$_2$H$_5$ | F | R$^{10}$ | 1 |
| 272 | 4-OCF$_3$ | F | R$^{11}$ | 1 |
| 273 | 4-OC$_2$H$_5$ | F | R$^{14}$ | 1 |
| 274 | 4-OC$_2$H$_5$ | OH | R$^1$ | 1 |
| 275 | 4-OC$_2$H$_5$ | OH | R$^3$ | 1 |
| 276 | 4-OC$_2$H$_5$ | OH | R$^{13}$ | 1 |
| 277 | 4-OC$_2$H$_5$ | OH | R$^2$ | 1 |
| 278 | 4-OC$_2$H$_5$ | OH | R$^5$ | 1 |
| 279 | 4-OC$_2$H$_5$ | OH | R$^6$ | 1 |
| 280 | 4-OC$_2$H$_5$ | OH | R$^{14}$ | 1 |
| 281 | 4-OC$_2$H$_5$ | OH | R$^9$ | 1 |
| 282 | 4-CH$_3$ | OH | R$^1$ | 1 |
| 283 | 3-F,4-OC$_2$H$_5$ | OH | R$^2$ | 1 |
| 284 | 4-C(CH$_3$)$_3$ | OH | R$^3$ | 1 |
| 285 | 4-(CH$_2$)$_2$CH$_3$ | OH | R$^3$ | 1 |
| 286 | 3,4-(CH$_2$)$_3$ | OH | R$^3$ | 1 |
| 287 | 4-F | OH | R$^3$ | 1 |
| 288 | 4-Cl | OH | R$^3$ | 1 |
| 289 | 4-Br | OH | R$^3$ | 1 |
| 290 | 3,4-(OCH$_2$O) | OH | R$^1$ | 1 |
| 291 | 3,4-(OCH$_2$O) | OH | R$^2$ | 1 |
| 292 | 4-OCH$_3$ | OH | R$^1$ | 1 |
| 293 | 4-OCH$_3$ | OH | R$^3$ | 1 |
| 294 | 4-CH$_2$OCH$_3$ | OH | R$^2$ | 1 |
| 295 | 4-CH$_2$OCH$_3$ | OH | R$^1$ | 1 |
| 296 | 4-OCF$_3$ | OH | R$^3$ | 1 |
| 297 | 4-OCF$_3$ | OH | R$^2$ | 1 |
| 298 | 4-OCF$_3$ | OH | R$^{11}$ | 1 |
| 299 | 4-CF$_3$ | OH | R$^1$ | 1 |
| 300 | 4-CF$_3$ | OH | R$^3$ | 1 |
| 301 | 4-OCF$_3$ | OH | R$^1$ | 1 |
| 302 | 3-F,4-OC$_2$H$_5$ | OH | R$^1$ | 1 |
| 303 | 4-OC$_2$H$_5$ | OH | R$^{11}$ | 1 |
| 304 | 4-OC$_2$H$_5$ | OH | R$^{12}$ | 1 |
| 305 | 4-Cl | OH | R$^1$ | 1 |
| 306 | 2,4-Cl$_2$ | OH | R$^2$ | 1 |
| 307 | 4-OC$_2$H$_5$ | OH | R$^4$ | 1 |
| 308 | 4-OC$_2$H$_5$ | OH | R$^7$ | 1 |
| 309 | 4-OC$_2$H$_5$ | OH | R$^8$ | 1 |
| 310 | 4-OC$_2$H$_5$ | OH | R$^{10}$ | 1 |
| 311 | 4-OC$_2$H$_5$ | OCOCH$_3$ | R$^3$ | 1 |
| 312 | 4-OC$_2$H$_5$ | OCH$_3$ | R$^3$ | 1 |
| 313 | 4-OCHF$_2$ | H | R$^1$ | 1 |
| 314 | 4-OCHF$_2$ | H | R$^2$ | 1 |
| 315 | 4-OCHF$_2$ | H | R$^3$ | 1 |
| 316 | 4-OCHF$_2$ | Cl | R$^1$ | 1 |
| 317 | 4-OCHF$_2$ | Cl | R$^2$ | 1 |
| 318 | 4-OCHF$_2$ | Cl | R$^3$ | 1 |
| 319 | 4-OCHF$_2$ | F | R$^1$ | 1 |
| 320 | 4-OCHF$_2$ | F | R$^2$ | 1 |
| 321 | 4-OCHF$_2$ | F | R$^3$ | 1 |
| 322 | 4-OCHF$_2$ | OH | R$^1$ | 1 |
| 323 | 4-OCHF$_2$ | OH | R$^2$ | 1 |
| 324 | 4-OCHF$_2$ | OH | R$^3$ | 1 |
| 325 | 4-OC$_2$H$_5$ | H | R$^1$ | 2 |
| 326 | 4-OC$_2$H$_5$ | H | R$^{13}$ | 2 |
| 327 | 4-OC$_2$H$_5$ | H | R$^2$ | 2 |
| 328 | 4-OC$_2$H$_5$ | H | R$^{11}$ | 2 |
| 329 | 4-OC$_2$H$_5$ | H | R$^6$ | 2 |
| 330 | 4-OC$_2$H$_5$ | H | R$^5$ | 2 |
| 331 | 4-OC$_2$H$_5$ | H | R$^{12}$ | 2 |
| 332 | 4-OC$_2$H$_5$ | H | R$^9$ | 2 |
| 333 | 4-OC$_2$H$_5$ | H | R$^4$ | 2 |
| 334 | 4-OC$_2$H$_5$ | H | R$^7$ | 2 |
| 335 | 4-OC$_2$H$_5$ | H | R$^{10}$ | 2 |
| 336 | 4-OC$_2$H$_5$ | H | R$^8$ | 2 |
| 337 | 3-F,4-OC$_2$H$_5$ | H | R$^2$ | 2 |
| 338 | 3-F,4-OC$_2$H$_5$ | H | R$^1$ | 2 |

TABLE I-continued

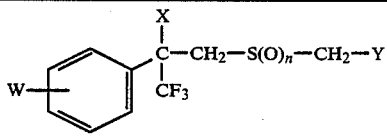

| COMPOUND NO. | W | X | Y | n |
|---|---|---|---|---|
| 339 | 4-Cl | H | $R^3$ | 2 |
| 340 | 4-Cl | H | $R^1$ | 2 |
| 341 | 2,4-$Cl_2$ | H | $R^1$ | 2 |
| 342 | 4-F | H | $R^3$ | 2 |
| 343 | 3,4-$(CH_2)_3$ | H | $R^3$ | 2 |
| 344 | 4-$(CH_2)_2CH_3$ | H | $R^3$ | 2 |
| 345 | 4-$C(CH_3)_3$ | H | $R^3$ | 2 |
| 346 | 4-$CH_3$ | H | $R^1$ | 2 |
| 347 | 4-$CH_2OCH_3$ | H | $R^2$ | 2 |
| 348 | 4-$CH_2OCH_3$ | H | $R^1$ | 2 |
| 349 | 4-$OCF_3$ | H | $R^3$ | 2 |
| 350 | 4-$OCF_3$ | H | $R^2$ | 2 |
| 351 | 4-$OCF_3$ | H | $R^1$ | 2 |
| 352 | 4-$OCF_3$ | H | $R^{11}$ | 2 |
| 353 | 4-$OCH_3$ | H | $R^3$ | 2 |
| 354 | 4-$OCH_3$ | H | $R^1$ | 2 |
| 355 | 3,4-$(OCH_2O)$ | H | $R^1$ | 2 |
| 356 | 3,4-$(OCH_2O)$ | H | $R^2$ | 2 |
| 357 | 4-$OC_2H_5$ | H | $R^3$ | 2 |
| 358 | 4-$CF_3$ | H | $R^1$ | 2 |
| 359 | 4-Br | H | $R^3$ | 2 |
| 360 | 4-$CF_3$ | H | $R^3$ | 2 |
| 361 | 4-$OC_2H_5$ | H | $R^{14}$ | 2 |
| 362 | 4-$OC_2H_5$ | Cl | $R^1$ | 2 |
| 363 | 4-$OC_2H_5$ | Cl | $R^{13}$ | 2 |
| 364 | 4-$OC_2H_5$ | Cl | $R^3$ | 2 |
| 365 | 4-$OC_2H_5$ | Cl | $R^{11}$ | 2 |
| 366 | 4-$OC_2H_5$ | Cl | $R^2$ | 2 |
| 367 | 4-$OC_2H_5$ | Cl | $R^5$ | 2 |
| 368 | 4-$OC_2H_5$ | Cl | $R^6$ | 2 |
| 369 | 4-$OC_2H_5$ | Cl | $R^{14}$ | 2 |
| 370 | 4-$OC_2H_5$ | Cl | $R^{12}$ | 2 |
| 371 | 4-$OC_2H_5$ | Cl | $R^9$ | 2 |
| 372 | 3-F,4-$OC_2H_5$ | Cl | $R^2$ | 2 |
| 373 | 3-F,4-$OC_2H_5$ | Cl | $R^1$ | 2 |
| 374 | 4-Cl | Cl | $R^3$ | 2 |
| 375 | 4-F | Cl | $R^3$ | 2 |
| 376 | 3,4-$(CH_2)_3$ | Cl | $R^3$ | 2 |
| 377 | 4-$(CH_2)_2CH_3$ | Cl | $R^3$ | 2 |
| 378 | 4-$C(CH_3)_3$ | Cl | $R^3$ | 2 |
| 379 | 4-$CH_3$ | Cl | $R^1$ | 2 |
| 380 | 4-$CH_2OCH_3$ | Cl | $R^2$ | 2 |
| 381 | 4-$CH_2OCH_3$ | Cl | $R^1$ | 2 |
| 382 | 4-$OCF_3$ | Cl | $R^3$ | 2 |
| 383 | 4-$OCF_3$ | Cl | $R^1$ | 2 |
| 384 | 4-$OCF_3$ | Cl | $R^2$ | 2 |
| 385 | 4-$OCF_3$ | Cl | $R^{11}$ | 2 |
| 386 | 4-$OCH_3$ | Cl | $R^3$ | 2 |
| 387 | 4-$OCH_3$ | Cl | $R^1$ | 2 |
| 388 | 3,4-$(OCH_2O)$ | Cl | $R^1$ | 2 |
| 389 | 3,4-$(OCH_2O)$ | Cl | $R^2$ | 2 |
| 390 | 4-Cl | Cl | $R^1$ | 2 |
| 391 | 2,4-$Cl_2$ | Cl | $R^1$ | 2 |
| 392 | 4-$CF_3$ | Cl | $R^1$ | 2 |
| 393 | 4-Br | Cl | $R^3$ | 2 |
| 394 | 4-$CF_3$ | Cl | $R^3$ | 2 |
| 395 | 4-$OC_2H_5$ | Cl | $R^4$ | 2 |
| 396 | 4-$OC_2H_5$ | Cl | $R^7$ | 2 |
| 397 | 4-$OC_2H_5$ | Cl | $R^8$ | 2 |
| 398 | 4-$OC_2H_5$ | Cl | $R^{10}$ | 2 |
| 399 | 4-$OC_2H_5$ | F | $R^1$ | 2 |
| 400 | 4-$OC_2H_5$ | F | $R^{11}$ | 2 |
| 401 | 4-$OC_2H_5$ | F | $R^3$ | 2 |
| 402 | 4-$OC_2H_5$ | F | $R^{13}$ | 2 |
| 403 | 4-$OC_2H_5$ | F | $R^2$ | 2 |
| 404 | 4-$OC_2H_5$ | F | $R^{12}$ | 2 |
| 405 | 4-Cl | F | $R^3$ | 2 |
| 406 | 4-$OCF_3$ | F | $R^1$ | 2 |
| 407 | 4-Br | F | $R^3$ | 2 |
| 408 | 4-$CF_3$ | F | $R^1$ | 2 |
| 409 | 4-Cl | F | $R^1$ | 2 |
| 410 | 2,4-$Cl_2$ | F | $R^1$ | 2 |

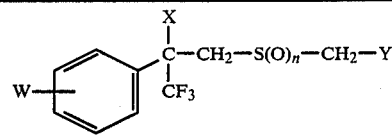

| COMPOUND NO. | W | X | Y | n |
|---|---|---|---|---|
| 411 | 4-$CH_3$ | F | $R^1$ | 2 |
| 412 | 4-$OCH_3$ | F | $R^1$ | 2 |
| 413 | 3-F,4-$OC_2H_5$ | F | $R^1$ | 2 |
| 414 | 3,4-$(OCH_2O)$ | F | $R^1$ | 2 |
| 415 | 4-$CH_2OCH_3$ | F | $R^1$ | 2 |
| 416 | 3-F,4-$OC_2H_5$ | F | $R^2$ | 2 |
| 417 | 3,4-$(OCH_2O)$ | F | $R^2$ | 2 |
| 418 | 4-$OCF_3$ | F | $R^2$ | 2 |
| 419 | 4-$CH_2OCH_3$ | F | $R^2$ | 2 |
| 420 | 4-F | F | $R^3$ | 2 |
| 421 | 4-$C(CH_3)_3$ | F | $R^3$ | 2 |
| 422 | 4-$OCH_3$ | F | $R^3$ | 2 |
| 423 | 4-$(CH_2)_2CH_3$ | F | $R^3$ | 2 |
| 424 | 3,4-$(CH_2)_3$ | F | $R^3$ | 2 |
| 425 | 4-$OCF_3$ | F | $R^3$ | 2 |
| 426 | 4-$CF_3$ | F | $R^3$ | 2 |
| 427 | 4-$OC_2H_5$ | F | $R^4$ | 2 |
| 428 | 4-$OC_2H_5$ | F | $R^5$ | 2 |
| 429 | 4-$OC_2H_5$ | F | $R^6$ | 2 |
| 430 | 4-$OC_2H_5$ | F | $R^7$ | 2 |
| 431 | 4-$OC_2H_5$ | F | $R^8$ | 2 |
| 432 | 4-$OC_2H_5$ | F | $R^9$ | 2 |
| 433 | 4-$OC_2H_5$ | F | $R^{10}$ | 2 |
| 434 | 4-$OCF_3$ | F | $R^{11}$ | 2 |
| 435 | 4-$OC_2H_5$ | F | $R^{14}$ | 2 |
| 436 | 4-$OC_2H_5$ | OH | $R^1$ | 2 |
| 437 | 4-$OC_2H_5$ | OH | $R^3$ | 2 |
| 438 | 4-$OC_2H_5$ | OH | $R^{13}$ | 2 |
| 439 | 4-$OC_2H_5$ | OH | $R^2$ | 2 |
| 440 | 4-$OC_2H_5$ | OH | $R^5$ | 2 |
| 441 | 4-$OC_2H_5$ | OH | $R^6$ | 2 |
| 442 | 4-$OC_2H_5$ | OH | $R^{14}$ | 2 |
| 443 | 4-$OC_2H_5$ | OH | $R^9$ | 2 |
| 444 | 4-$CH_3$ | OH | $R^1$ | 2 |
| 445 | 3-F,4-$OC_2H_5$ | OH | $R^2$ | 2 |
| 446 | 4-$C(CH_3)_3$ | OH | $R^3$ | 2 |
| 447 | 4-$(CH_2)_2CH_3$ | OH | $R^3$ | 2 |
| 448 | 3,4-$(CH_2)_3$ | OH | $R^3$ | 2 |
| 449 | 4-F | OH | $R^3$ | 2 |
| 450 | 4-Cl | OH | $R^3$ | 2 |
| 451 | 4-Br | OH | $R^3$ | 2 |
| 452 | 3,4-$(OCH_2O)$ | OH | $R^1$ | 2 |
| 453 | 3,4-$(OCH_2O)$ | OH | $R^2$ | 2 |
| 454 | 4-$OCH_3$ | OH | $R^1$ | 2 |
| 455 | 4-$OCH_3$ | OH | $R^3$ | 2 |
| 456 | 4-$CH_2OCH_3$ | OH | $R^2$ | 2 |
| 457 | 4-$CH_2OCH_3$ | OH | $R^1$ | 2 |
| 458 | 4-$OCF_3$ | OH | $R^3$ | 2 |
| 459 | 4-$OCF_3$ | OH | $R^2$ | 2 |
| 460 | 4-$OCF_3$ | OH | $R^{11}$ | 2 |
| 461 | 4-$CF_3$ | OH | $R^1$ | 2 |
| 462 | 4-$CF_3$ | OH | $R^3$ | 2 |
| 463 | 4-$OCF_3$ | OH | $R^1$ | 2 |
| 464 | 3-F,4-$OC_2H_5$ | OH | $R^1$ | 2 |
| 465 | 4-$OC_2H_5$ | OH | $R^{11}$ | 2 |
| 466 | 4-$OC_2H_5$ | OH | $R^{12}$ | 2 |
| 467 | 4-Cl | OH | $R^1$ | 2 |
| 468 | 2,4-$Cl_2$ | OH | $R^2$ | 2 |
| 469 | 4-$OC_2H_5$ | OH | $R^4$ | 2 |
| 470 | 4-$OC_2H_5$ | OH | $R^7$ | 2 |
| 471 | 4-$OC_2H_5$ | OH | $R^8$ | 2 |
| 472 | 4-$OC_2H_5$ | OH | $R^{10}$ | 2 |
| 473 | 4-$OC_2H_5$ | $OCOCH_3$ | $R^3$ | 2 |
| 474 | 4-$OC_2H_5$ | $OCH_3$ | $R^3$ | 2 |
| 475 | 4-$OCHF_2$ | H | $R^1$ | 2 |
| 476 | 4-$OCHF_2$ | H | $R^2$ | 2 |
| 477 | 4-$OCHF_2$ | H | $R^3$ | 2 |
| 478 | 4-$OCHF_2$ | Cl | $R^1$ | 2 |
| 479 | 4-$OCHF_2$ | Cl | $R^2$ | 2 |
| 480 | 4-$OCHF_2$ | Cl | $R^3$ | 2 |
| 481 | 4-$OCHF_2$ | F | $R^1$ | 2 |
| 482 | 4-$OCHF_2$ | F | $R^2$ | 2 |

TABLE I-continued

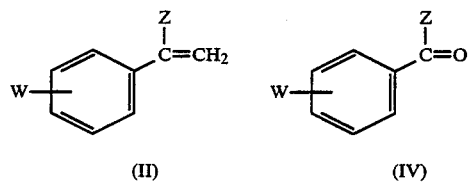

| COMPOUND NO. | W | X | Y | n |
|---|---|---|---|---|
| 483 | 4-OCHF$_2$ | F | R$^3$ | 2 |
| 484 | 4-OCHF$_2$ | OH | R$^1$ | 2 |
| 485 | 4-OCHF$_2$ | OH | R$^2$ | 2 |
| 486 | 4-OCHF$_2$ | OH | R$^3$ | 2 |

It will be appreciated that in all of the above compounds there exists the possibility of steroismerism due to asymmetric substitution at the benzylic carbon atom of the compounds of formula IA. All of the compounds listed in Table I are in form of racemic mixtures of the two optically active isomers (the R- and S- isomers). It is to be understood that the invention includes within its scope not only isomer mixtures including racemic mixtures, but also any single isomer of an invention compound.

The compounds of formula IA wherein X is hydrogen and n has the value 0 may be prepared by the reaction of a styrene of formula II with a thioalcohol of formula YCH$_2$SH (III) in the presence of a radical initiator or a base. The styrenes of formula II may be prepared by the Wittig reaction of methyltriphenylphosphonium bromide with an acetophenone of formula IV in the presence of a base, for example n-butyllithium. These steps are summarised in Scheme I.

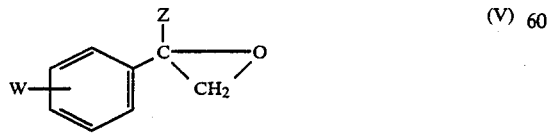

(II)          (IV)

Those compounds of formula IV wherein Z represents trifluoromethyl and W represents trifluoromethoxy or ethoxy have not been previously described. Accordingly, in a further aspect, the invention provides 1,1,1-tri-fluoro-2-(4-ethoxyphenyl)prop-2-ene and 1,1,1-trifluoro-2-(4-trifluoromethoxyphenyl)prop-2-ene.

The compounds of formula IA wherein X is hydroxy and n has the value 0 may be prepared by the reaction between an epoxide of formula V and a thioalcohol of formula III in the presence of a base. The epoxides of formula V are conveniently prepared from acetophenones of formula IV by the action of trimethylsulphoxonium iodide in the presence of a base, for example potassium hydroxide in t-butanol. These steps are summarised in Scheme II.

(V)

The compounds of formula IA wherein X is halogen, alkoxy or acyloxy, and n has the value 0 may be prepared from the corresponding hydroxy compound described above (i.e., the compounds of formula IA wherein X is hydroxy) by reaction with halogenating, alkylating or acylating agents. Examples of these reactions are illustrated in Scheme III.

Any of the compounds of formula IA wherein n has the value 0 may be converted to those compounds wherein n has the value 1 or 2 by reaction with oxidising agents, such as meta-chloroperbenzoic acid or hydrogen peroxide; these procedures are summarised in Scheme IV.

Further details of these processes are set forth in the Examples hereinafter.

Scheme I

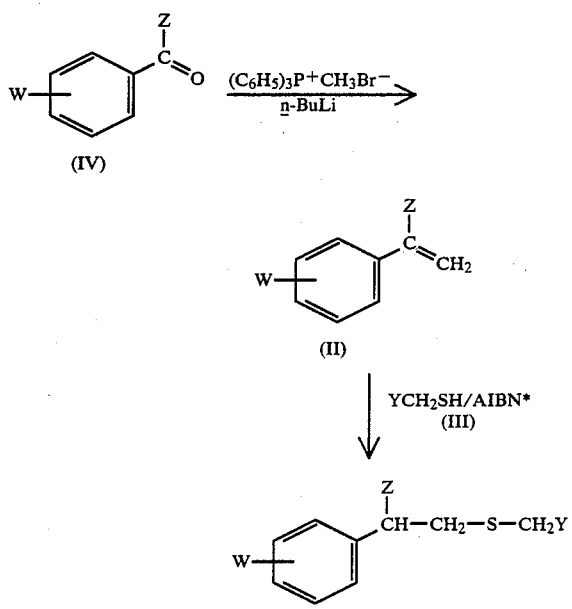

*AIBN = α,α'-Azo-bis-isobutyronitrile (radical initiator)

Scheme II

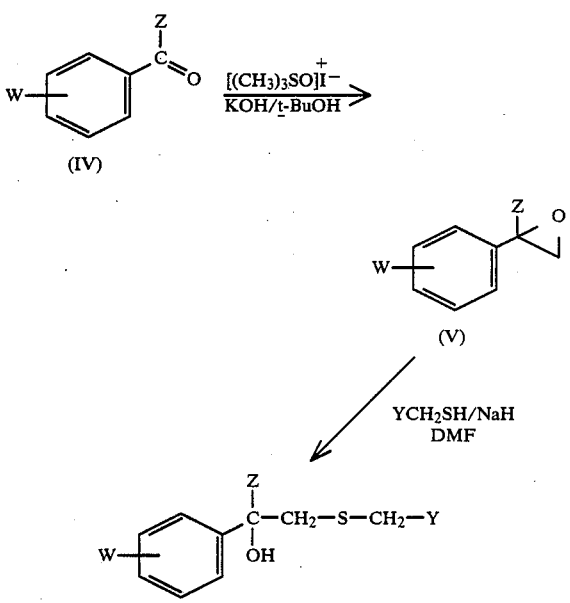

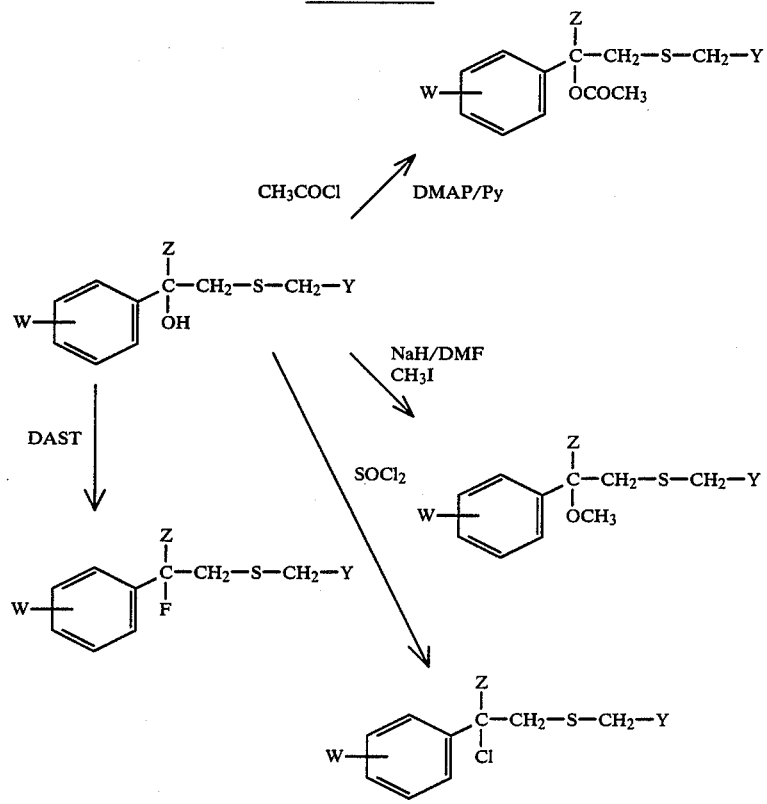

Key:
DAST = Diethylaminosulphur trifluoride
DMAP = Dimethylaminopyridine
Py = Pyridine
DMF = Dimethylformamide

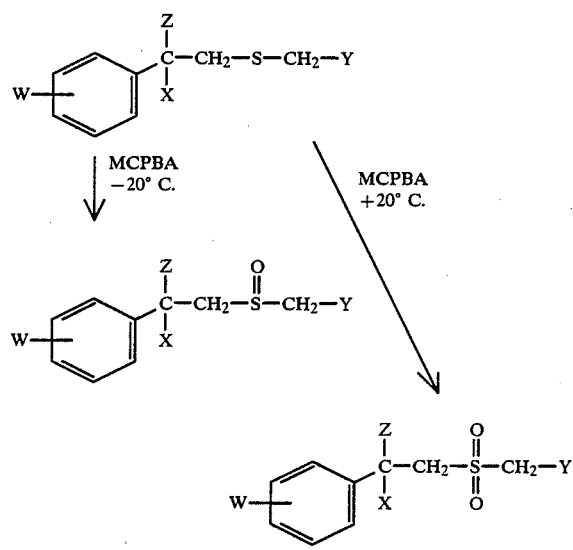

MCPBA = meta-chloroperbenzoic acid

The compounds of formula I may be used to combat and control infestations of insect pests and also other invertebrate pests, for example, acarine pests. The insect and acarine pests which may be combated and controlled by the use of the invention compounds include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula I suitable inert diluent or carrier materials, and/or surface active agents.

The compounds of the invention may be the sole active ingredient of the composition or they may be admixed with one or more additional active ingredients such as insecticides, insecticide synergists, herbicides, fungicides or plant growth regulators where appropriate.

Suitable additional active ingredients for inclusion in admixture with the compounds of the invention may be compounds which will broaden the spectrum of activity of the compounds of the invention or increase their persistence in the location of the pest. They may synergise the activity of the compounds of the invention or complement the activity for example by increasing the speed of effect, improving knockdown or overcoming repellency. Additionally multi-component mixtures of this type may help to overcome or prevent the development of resistance to individual components.

The particular insecticide, herbicide or fungicide included in the mixture will depend upon its intended utility and the type of complementary action required. Examples of suitable insecticides include the following:

(a) Pyrethroids such as permethrin, esfenvalerate, deltamethrin, cyhalothrin, biphenthrin, fenpropathrin, cyfluthrin, tefluthrin, fish safe pyrethroids for example ethofenprox, natural pyrethrin, tetramethrin, s-bioallethrin, fenfluthrin, prallethrin or 5-benzyl-3-furylmethyl-(E)-(1R, 3S)-2,2-dimethyl-3-(2-oxothiolan-3-ylidenemethyl)cyclopropane carboxylate;

(b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathion, chlorpyrifos, phosalone, fensulfothion, fonofos, phorate, phoxim, pyrimiphos-methyl, fenitrothion or diazinon;

(c) Carbamates (including aryl carbamates) such as pirimicarb, cloethocarb, carbofuran, ethiofencarb, aldicarb, thiofurox, carbosulfan, bendiocarb, fenobucarb, propoxur or oxamyl;

(d) Benzoyl ureas such as triflumuron, chlorofluazuron;

(e) Organic tin compounds such as cyhexatin, fenbutatin oxide, azocyclotin;

(f) Macrolides such as avermectins or milbemycins, for example abamectin, avermectin, and milbemycin;

(g) Hormones such as juvenile hormone, juvabione, or ecdysones.

(h) Pheromones.

(i) Organochlorine compounds such as benzene hexachloride, DDT, chlordane, endosulfan or dieldrin.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin, can be employed. Alternatively insecticides specific for particular insect species/stages for example ovolarvicides such as clofentezine, flubenzimine, hexythiazox and tetradifon, motilicides such as dicofol or propargite, acaricides such as bromopropylate, chlorobenzilate, or insect growth regulators such as hydramethylon, cyromazin, methoprene, chlorofluazuron and diflubenzuron may also be included in the compositions.

Examples of suitable insecticide synergists for use in the compositions include piperonyl butoxide, sesamex, and dodecyl imidazole.

Suitable herbicides, fungicides and plant growth regulators for inclusion in the compositions will depend upon the intended target and the effect required. An example of a rice selective herbicide which can be included is propanil, an example of a plant growth regulator for use in cotton is "Pix", and examples of fungicides for use in rice include blasticides such as blasticidin-S. The choice of other ingredients to be used in mixture with the active ingredient will often be within the normal skill of the formulator, and will be made from known alternatives depending upon the total effect to be achieved.

The ratio of the compound of the invention to any other active ingredient in the composition will depend upon a number of factors including the type of insect pests to be controlled, and the effects required from the mixture. However in general, the additional active ingredient of the composition will be applied at about the rate it would usually be employed if used on its own, or at a lower rate if synergism occurs.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material, for example pumice.

Alternatively the compositions may be in the form of liquid preparations to be used as aerosols, dips or sprays. Dips and sprays are generally aqueous dispersions or emulsions of the active ingredient in the presence of one or more known wetting agents, dispersing agents or emulsifying agents (surface active agents). Aerosol compositions may contain the active ingredient or ingredients, a propellant and an inert diluent, for example odourless kerosene or alkylated benzenes.

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters or sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents.

Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydrofurfuryl alcohol (THFA).

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogenous for a sufficient time to enable them to be applied by conventional spray equipment. The concentrates may contain 10–85% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compositions of the invention are very toxic to wide varieties of insect and other invertebrate pests, including, for example, the following:

*Myzus persicae* (aphids)
*Aphis fabae* (aphids)
*Megoura viceae* (aphids)
*Aedes aegypti* (mosquitos)
Anopheles spp. (mosquitos)
Culex spp. (mosquitos)
*Dysdercus fasciatus* (capsids)
*Musca domestica* (houseflies)
*Pieris brassicae* (white butterfly, larvae)
*Plutella maculipennis* (diamond back moth, larvae)
*Phaedon cochleariae* (mustard beetle)
*Tetranychus cinnabarinus* (carmine spider mite)
*Tetranychus urticae* (red spider mites)
Aonidiella spp. (scale insects)
Trialeuroides spp. (white flies)
*Blattella germanica* (cockroaches)
*Blatta orientalis* (cockroaches)
*Periplaneta americana* (cockroaches)
*Spodoptera littoralis* (cotton leaf worm)
*Heliothis virescens* (tobacco budworms)
*Chortiocetes terminifera* (locusts)
Diabrotica spp. (rootworms)
Agrotis spp. (cutworms)
*Chilo partellus* (maize stem borers)
*Nilaparvata lugens* (plant hoppers)
*Nephotettix cincticeps* (leaf hoppers)
*Chilo suppressalis* (stem borers)
*Chilo partellus* (stem borers)
*Panonychus ulmi*
*Panonychus citri*

In addition to providing effective control of lepidopteran pests of cotton, for example Spodoptera spp. and Heliothis spp, the compounds of formula (I) and compositions comprising them have also been shown to be particularly useful in the control of pests of maize and rice such as Chilo spp. (stem borers), Nilaparvata spp. and Nephotettix spp. (plant and leaf hoppers). Some of the compounds show high levels of activity against rice pests at rates which are not toxic to fish, thus enabling their use in paddy rice where fish are cultivated in the paddy.

The compounds of formula (I) and compositions comprising them may also be useful in combating insect and acarine pests which infest domestic animals, such as *Lucilia sericata*, and ixodid ticks such as Boophilus spp., Ixodes spp., Amblyomma spp., Rhipicephalus spp; and Dermaceutor spp. They are effective in combating both susceptible and resistant strains of these pests in their adult, larval and intermediate stages of growth, and may be applied to the infested host animal by topical, oral or parenteral administration.

The following Examples illustrate various aspects of this invention. In the preparation Examples the products were usually identified and characterised by means of nuclear magnetic reasonance spectroscopy and infrared spectroscopy. In each case where a product is specifically named its spectral characteristics are consistent with the assigned structure. Except where stated otherwise, exemplified compounds having one or more asymmetrically substituted carbon atoms were prepared in racemic form.

In the Examples, Gas Liquid Chromatography (GLC) retention times were determined on a Hewlett Packard 5890 Gas Chromatograph, using a Chrompak, CPSil 5CB column of 12.5 m length and 0.2 mm internal diameter. Unless otherwise stated, the injection temperature was 100° C., and a temperature gradient of 15° C./minute employed, up to a maximum temperature of 280° C., maintained for 4 minutes. The carrier gas was helium at a column head pressure maintained at 11 psi. Alternative injection and maximum temperature are indicated in the Examples where appropriate.

$^1$H Nuclear Magnetic Resonance (NMR) spectrometry was performed at a frequency of 270 MHz on a Jeol FX 270 NMR spectrometer, unless otherwise indicated. 90 MHz, 60 MH$_z$ and 400 MH$_z$ $^1$H NMR spectrometry were performed using Jeol FX 90 Q, Jeol PMX60 SI and Jeol GX400 spectrometers respectively. $^{19}$F NMR spectrometry was performed on a Jeol FX90Q spectrometer at a frequency of 84.26 MHz. All NMR shift values ($\delta$) are quoted in ppm relative to a standard (TMS or CFCl$_3$).

Molecular Ion (M$^+$) peaks (measured in atomic mass units) were determined on one of three mass spectrometers: Jeol DX303, Kratos MS80 or Hewlett Packard HP 5992.

EXAMPLE 1

This Example illustrates the preparation of 4-ethoxy-α,α,α-trifluoroacetophenone.

A. From trifluoroacetic acid

Literature reference: Journal of Organic Chemistry, 32, 1311, (1967).

A solution of 4-bromo-ethoxybenzene (60 g) in diethyl ether (100 cm$^3$) was added slowly to a stirred mixture of magnesium turnings (7.4 g), diethyl ether (50 cm$^3$) and a crystal of iodine (ca. 0.5 g) under a nitrogen atmosphere. After ca. 15 cm$^3$ of the solution had been added the mixture was warmed gently until the reaction commenced and the rate of addition was thereafter adjusted to maintain a gentle reflux. After the completion of the addition (ca. 30 minutes) the mixture was stirred for a further 20 minutes at the ambient temperature (ca. 22° C.), following which a solution of trifluoroacetic acid (12.0 g) in diethyl ether (25 cm$^3$) was added dropwise over a period of one hour. The mixture was then heated at the reflux temperature for a further one hour after which the mixture was poured into crushed ice and acidified with concentrated hydrochloric acid. The organic layer was separated, and the aqueous layer extracted three times with diethyl ether. The extracts were combined with the organic layer, and the ethereal solution washed twice with saturated sodium bicarbonate, and dried over anhydrous sodium sulphate. After removal of the solvent by evaporation under reduced pressure the residual oil (48 g) was subjected to fractional distillation. Three fractions were collected at 64° C./0.1–0.2 mg Hg, containing 1.2 g (75% pure by gas-liquid chromatography), 13 g (91% pure) and 2.4 g (85% pure) of 4-ethoxytrifluoroacetophenone respectively. The major fraction was used without further purification.

$^1$H NMR (CDCl$_3$) $\delta$: 1.46 (3H,t); 4.15 (2H,q); 7.0 (2H,m); 8.05 (2H,m).

17

Infra red (liquid film): 1710 cm$^{-1}$.

B. From trifluoroacetic anhydride

A solution of 4-bromoethoxybenzene (150 g) in diethyl ether (200 cm$^3$) was added slowly to a stirred mixture of magnesium turnings (20.0 g), diethyl ether (50 cm$^3$) and a crystal of iodine (ca. 0.5 g) under a nitrogen atmosphere. After ca. 35 cm$^3$ of the solution had been added the mixture was warmed gently until the reaction commenced and the rate of addition was adjusted to maintain a gentle reflux. After the addition was complete the mixture was stirred for a further one hour at the ambient temperature (ca. 22° C.) after which the mixture was cooled at 0° C. by external cooling and a solution of trifluoroacetic anhydride (203 g) in diethyl ether (100 cm$^3$) was added, initially drop by drop, and then at a faster rate so as to maintain a gentle reflux. The addition was completed over a period of 20 minutes after which the mixture was stirred for a further 45 minutes. The mixture was then poured onto crushed ice and the product worked up in the manner set out in Part A above, to give, after distillation, 4-ethoxytrifluoroacetophenone (35 g).

EXAMPLE 2

By the use of a procedure similar to that set out in part B of Example 1 above, 4-trifluoromethoxy-α,α,α-trifluoroacetophenone was prepared from 4-bromotrifluoromethoxybenzene and trifluoroacetic anhydride.

In this case, the product was purified by distillation in a Kugelrohr apparatus under reduced pressure (ca 12 mmHg), at an oven temperature of 50°–70° C.

$^1$H NMR (CDCl$_3$) δ (ppm): 7.35, 8.14 (4H,d);
$^{19}$F NMR (CDCl$_3$) δ (ppm relative to CFCl$_3$):
−58.1 (CF$_3$O, s);
−72.1 (CF$_3$, s).

IR (liquid film): 1730, 1610, 1270, 1250–1150 cm$^{-1}$.

EXAMPLE 3

This Example illustrates the preparation of 1,1,1-trifluoro-2-(4-ethoxyphenyl)prop-2-ene oxide.

Trimethylsulphoxonium iodide (8.1 g) was added to a stirred solution of 4-ethoxy-α,α,α-trifluoroacetophenone (8 g) in t-butanol (25 cm$^3$). When the addition was complete, potassium hydroxide pellets (2 g) were added, and the reaction mixture was heated at the reflux temperature for one hour. The mixture was cooled, and poured into a dilute aqueous solution of hydrochloric acid. The aqueous mixture was extracted eight times with diethyl ether and the combined extracts were dried over anhydrous magnesium sulphate. Removal of the solvent by evaporation under reduced pressure gave a pale yellow oil (5.5 g) containing a small amount of solid residue. The crude product residue was passed through a plug of silica gel, using n-hexane containing 10% by volume ethyl acetate as eluent. Further purification by chromatography using a silica gel column eluted with n-hexane containing 10% by volume ethyl acetate gave two fractions containing 1,1,1-trifluoro-2-(4-ethoxyphenyl)prop-2-ene oxide. The first fraction was shown by gas liquid chromatography to be 79% pure, the second 98% pure.

$^1$H NMR (CDCl$_3$) δ (ppm): 1.42 (3H,t); 2.9 (1H,dq); 3.38 (1H,d); 4.07 (2H,q); 6.9, 7.4 (4H,m).

EXAMPLE 4

By the use of a procedure similar to that set out in Example 3 above, 1,1,1,-trifluoro-2-(4-trifluoromethoxyphenyl)prop-2-ene oxide was prepared from 4-trifluoromethoxy-α,α,α,-trifluoroacetophenone.

GLC retention time: 2.34 minutes (50° C.–280° C. run).

EXAMPLE 5

This example illustrates the preparation of 1,1,1-trifluoro-2-(4-ethoxyphenyl)-2-hydroxyprop-3-yl 3-phenoxybenzyl sulphide, Compound No. 112.

To a suspension of sodium hydride (0.1 g) in N,N-dimethylformamide (10 cm$^3$) at 0° C. was added 3-phenoxybenzyl thiol (0.28 g). After stirring for 30 minutes, 1,1,1-trifluoro-2-(4-ethoxyphenyl)-prop-2-ene oxide (0.3 g) was added. The reaction mixture was stirred for ten minutes before being added to water (25 cm$^3$) and neutralised with acetic acid. The product was extracted into diethyl ether (200 cm$^3$). The organic layer was dried over anhydrous sodium sulphate and the solvent removed by evaporation under reduced pressure. The resulting oil was purified by chromatography to give 1,1,1-trifluoro-2-(4-ethoxyphenyl)-2-hydroxyprop-3-yl 3-phenoxybenzyl sulphide as a colourless oil (0.4 g).

$^1$H NMR (CDCl$_3$) δ (ppm): 1.4 (3H,t); 3.2 (2H, ABq); 3.5 (2H,ABq and 1H,s); 4.0 (2H,q); 7.1 (13H,m).

GLC retention time: 12.84 minutes.

EXAMPLE 6

By a process similar to that described in Example 5, 1,1,1-trifluoro-2-(4-ethoxyphenyl)-2-hydroxyprop-3-yl 6-phenoxy-2-pyridylmethyl sulphide, Compound No. 141, was prepared from 1,1,1-trifluoro-2-(4-ethoxyphenyl)prop-2-ene oxide and 6-phenoxy-2-pyridylmethylthiol.

$^1$H NMR (CDCl$_3$) δ (ppm): 7.1 (12H,m); 6.2 (1H,s); 4.0 (2H,q); 3.6 (2H,m); 3.2 (2H,m); 1.4 (3H,t).

GLC retention time: 12.30 minutes.

EXAMPLE 7

This example illustrates the preparation of 1,1,1,2-tetrafluoro-2-(4-ethoxyphenyl)prop-3-yl 3-phenoxybenzyl sulphide, Compound No. 75.

To a solution of diethylaminosulphur trifluoroide (0.043 g) in dichloromethane (5 cm$^3$) at −78° C. was added a solution of 1,1,1-trifluoro-2-(4-ethoxyphenyl)-2-hydroxyprop-3-yl 3-phenoxybenzyl sulphide (0.1 g) in dichloromethane (2 cm$^3$). The reaction mixture was warmed to −40° C. for 110 minutes, then cooled to −78° C. prior to the addition of a saturated aqueous solution of sodium bicarbonate (1.5 cm$^3$). The reaction mixture was allowed to warm to room temperature and the organic layer was separated. The aqueous layer was extracted with dichloromethane (3×8 cm$^3$) and the organic layers combined. Silica gel (1 g) was added, and the solvent was evaporated under reduced pressure. The residue was purified by chromatography on a silica gel support, eluting with petroleum ether containing 10% by volume diethyl ether, to give 1,1,1,2-tetrafluoro-2-(4-ethoxyphenyl)prop-3-yl 3-phenoxybenzyl sulphide as a colourless oil (0.062 g).

90 MHZ $^1$H NMR (CDCl$_3$) δ (ppm): 1.4 (3H,t), 3.1 (2H,ABx); 3.5 (2H,ABq); 4.0 (2H,q); 7.1 (13H,m).

GLC retention time: 11.95 minutes

EXAMPLE 8

By a process similar to that described in Example 7, 1,1,1,2-tetrafluoro-2-(4-ethoxyphenyl)prop-3-yl 6-phenoxy-2-pyridylmethyl sulphide, Compound No. 76, was prepared from 1,1,1-trifluoro-2-(4-ethoxyphenyl)-2-hydroxyprop-3-yl 6-phenoxy-2-pyridylmethyl sulphide.

$^1$H NMR (CDCl$_3$) δ (ppm): 7.1 (12H,m); 4.0 (2H,q); 3.4 (2H,m); 3.3 (2H,m); 1.4 (3H,t).

GLC retention time: 11.51 minutes.

EXAMPLE 9

This example illustrates the preparation of 1,1,1-trifluoro-2-chloro-2-(4-ethoxyphenyl)prop-3-yl 3-phenoxybenzyl sulphide, Compound No. 38.

Thionyl chloride (0.2 g) was added to a cooled solution of 1,1,1-trifluoro-2-(4-ethoxyphenyl)-2-hydroxyprop-3-yl 3-phenoxybenzyl sulphide (0.165 g) and imidazole (0.123 g) in acetonitrile (5 cm$^3$), the temperature of the mixture being maintained at 0° C. The reaction mixture was then allowed to warm to the ambient temperature (21° C.) and stirred for 30 minutes, before being added to a saturated aqueous solution of sodium bicarbonate (7 cm$^3$). The product was extracted into diethyl ether (3×15 cm$^3$), and the combined organic layers were dried over anhydrous magnesium sulphate and evaporated under reduced pressure. The residue was purified by chromatography on a silica gel support, eluting with petroleum ether containing 10% by volume diethy ether, to give 1,1,1-trifluoro-2-chloro-2-(4-ethoxyphenyl)prop-3-yl 3-phenoxybenzyl sulphide (0.12 g) as a colourless oil.

90 MHz $^1$H NMR (CDCl$_3$) δ (ppm): 1.4 (3H,t); 3.2 (2H,ABq); 3.6 (2H,s); 4.0 (2H,q); 7.1 (13H,m).

$^{19}$F NMR (CDCl$_3$) δ (ppm - relative to CFCl$_3$): −75.8 (CF$_3$,s).

GLC retention time: Product decomposed.

EXAMPLE 10

This example illustrates the preparation of 1,1,1-trifluoro-2-(4-ethoxyphenyl)prop-2-ene.

To a suspension of methyltriphenylphosphonium bromide (5.1 g) in tetrahydrofuran (15 cm$^3$) maintained at 0° C. was added n-butyllithium (6.1 cm$^3$ of a 2.5 molar solution in n-hexane). The resulting solution was stirred for fifteen minutes prior to the addition of a solution of 4-ethoxy-α,α,α-trifluoroacetophenone (2.5 g) in tetrahydrofuran (10 cm$^3$). The reaction mixture was stirred for 45 minutes before quenching by dilution with a saturated aqueous solution of ammonium chloride. The product was extracted into diethyl ether (3×20 cm$^3$) and the combined organic layers were evaporated under reduced pressure. The residual pale brown oil was washed through a plug of silica, eluting with n-hexane. Evaporation of the solvent under reduced pressure and distillation in a Kugelrohr apparatus at an oven temperature of 170° C. gave 1,1,1-trifluoro-2-(4-ethoxyphenyl)prop-2-ene as a pale yellow oil (0.95 g).

90 MHz $^1$H NMR (CDCl$_3$) δ (ppm): 1.4 (3H,t); 4.0 (2H,q); 5.7 (1H,m); 5.8 (1H,m); 6.9 (2H,d); 7.4 (2H,d).

EXAMPLE 11

By a process similar to that described in Example 10, 1,1,1-trifluoro-2-(4-trifluoromethoxyphenyl)prop-2-ene was prepared from 4-trifluoromethoxy-α,α,α-trifluoroacetophenone.

In view of its high volatility, this product was not isolated.

EXAMPLE 12

The example illustrates the preparation of 1,1,1-trifluoro-2-(4-ethoxyphenyl)prop-3-yl 3-phenoxybenzyl sulphide, Compound No. 1.

A mixture of 1,1,1-trifluoro-2-(4-ethoxyphenyl)prop-2-ene (0.1 g), 3-phenoxybenzylthiol (0.1 g) and α,α'-azobis isobutyronitrile (0.02 g) was heated at 90° C. for 1 hour. After cooling, the reaction mixture was purified by high performance liqud chromatography on a silica gel support, using n-hexane containing 1% by volume ethyl acetate as eluent, to give 1,1,1-trifluoro-2-(4-ethoxyphenyl)prop-3-yl 3-phenoxybenzyl sulphide (0.06 g) as a colourless oil.

$^1$H NMR (CDCl$_3$) δ (ppm): 1.4 (3H,t); 2.9 (2H,m); 3.3 (1H,m); 3.5 (2H,ABq); 4.0 (2H,q); 7.1 (13H,m). $^{19}$F NMR (CDCl$_3$) δ (ppm relative to CFCl$_3$): −70 ppm.

GLC retention time: 11.79 minutes.

EXAMPLE 13

By a process similar to that described in Example 12, 1,1,1-trifluoro-2-(4-trifluoromethoxyphenyl)prop-3-yl 3-phenoxybenzyl sulphide, Compound No. 27, was prepared from 1,1,1-trifluoro-2-(4-trifluoromethoxyphenyl)prop-2-ene and 3-phenoxybenzylthiol.

$^1$H NMR (CDCl$_3$) δ (ppm): 7.1 (13H,m); 3.6 (2H,m); 3.4 (1H,m); 2.9 (2H,m).

GLC retention time: 9.80 minutes.

EXAMPLE 14

By a process similar to that described in Example 12, 1,1,1-trifluoro-2-(4-ethoxyphenyl)prop-3-yl 6-phenoxy-2-pyridylmethyl sulphide, Compound No. 4, was prepared from 1,1,1-trifluoro-2-(4-ethoxyphenyl)prop-2-ene and 6-phenoxy-2-pyridylmethythiol.

$^1$H NMR (CDCl$_3$) δ (ppm): 7.1 (12H,m); 4.0 (2H,q); 3.7 (2H,m); 3.4 (1H,m); 3.0 (2H,m); 1.4 (3H,t).

GLC retention time: 11.56 minutes.

EXAMPLE 15

This example illustrates the preparation of 1,1,1,2-tetrafluoro-2-(4-ethoxyphenyl)prop-3-yl 6-phenoxy-2-pyridylmethyl sulphoxide, Compound No. 238.

A solution of 1,1,1,2-tetrafluoro-2-(4-ethoxyphenyl)prop-3-yl 6-phenoxy-2-pyridylmethyl sulphide (0.1 g) in dichloromethane (7 cm$^3$) was cooled to −30° C. and meta-chloroperbenzoic acid (0.078 g) was added. The solution was allowed to warm to −20° C., and was stirred at this temperature for 30 minutes. Silical gel (3 g) was added to the reaction mixture and the solvent was then evaporated under reduced pressure. The residue was applied to a silica gel column, and eluted with diethyl ether containing 30% petroleum ether. Evaporation of the major product containing fraction gave 1,1,1,2-tetrafluoro-2-(4-ethoxyphenyl)prop-3-yl 6-phenoxy-2-pyridylmethyl sulphoxide as a colourless oil (0.095 g).

$^1$H NMR (CDCl$_3$) δ (ppm): 1.4 (3H,t); 3.3 (1H,m) 4.0 (5H, including 2H,q and 3H,m); 7.1 (12H,m).

GLC retention time: Product decomposed.

EXAMPLE 16

This example illustrates the preparation of 1,1,1,2-tetrafluoro-2-(4-ethoxyphenyl)prop-3-yl 6-phenoxy-2-pyridylmethyl sulphone, Compound No. 400.

Meta-chloroperbenzoic acid (0.16 g) was added to a solution of 1,1,1,2-tetrafluoro-2-(4-ethoxyphenyl)prop-3-yl 6-phenoxy-2-pyridylmethyl sulphide (0.1 g) in dichloromethane (10 cm³), maintained at a temperature of −20° C. by external cooling. The reaction mixture was allowed to warm to the ambient temperature (ca 20° C.) and, after stirring for 110 minutes, was poured into a saturated aqueous solution of sodium bicarbonate (10 cm³). The resultant mixture was extracted with dichloromethane (3×15 cm³), the organic layers were combined, and the solvent evaporated under reduced pressure. Chromatography of the residual oil on a silica gel support, using petroleum ether containing 25% by volume diethyl ether as eluent gave 1,1,1,2-tetrafluoro-2-(4-ethoxyphenyl)prop-3-yl 6-phenoxy-2-pyridylmethyl sulphone (0.09 g) as a colourless oil.

¹H NMR (CDCl₃) δ (ppm): 1.4 (3H,t); 3.9 (6H including 2H,q and 4H,m); 7.2 (12H,m).

EXAMPLE 17

This Example illustrates the insecticidal properties of the Products of this invention.

The activity of the Product was determined using a variety of insect pests. The Product was used in the form of liquid preparations containing 500, 250 or 100 parts per million (ppm) by weight of the Product. The preparations were made by dissolving the Product in acetone and diluting the solutions with water containing 0.01% by weight of a wetting agent sold under the trade name "LISSAPOL" NX until the liquid preparations contained the required concentration of the Product. "Lissapol" is a Registered Trade Mark.

The test procedure adopted with regard to each pest was basically the same and comprised supporting a number of the pests on a medium which was usually a host plant or a foodstuff on which the pests feed, and treating either or both the pests and the medium with the preparations. The mortality of the pests was then assessed at periods usually varying from one to three days after the treatment.

In the case of the species *Musca domestica* (housefly), additional tests to determine the knockdown effect of the compounds were performed. Details are given in Table II.

The results of the tests are given in Table III for each of the Products, at the rate in parts per million given in the second column, as a grading of mortality designated as A, B or C wherein A indicates 80–100% mortality or knockdown (70–100% in the case of *Spodoptera exigua*), B indicates 50–79% mortality or knockdown (50–69% in the case of *Spodoptera exigua*) and C indicates less than 50% mortality or knockdown.

In Table III the pest organism used is designated by a letter code and the pest species, the support medium or food, and the type and duration of test is given in Table II.

Each product in Table III is identified by the letter assigned to it in Examples 1 to 16.

TABLE II

| CODE LETTERS | TEST SPECIES | COMMON NAME | GROWTH STAGE | SUPPORT MEDIUM/FOOD | TYPE OF TEST | DURATION DAYS |
|---|---|---|---|---|---|---|
| MP | *Myzus persicae* | Peach/Potato aphid | Adult/Nymph | Chinese cabbage leaf | Contact | 3 |
| NL | *Nilaparavata lugens* | Brown planthopper | Nymph | Rice plant | Contact | 3 |
| MD | *Musca domestica* (WHO strain) | Housefly | Adult | Plastic pot/Cotton wool and sugar solution | Contact | 1 |
| MD/K | *Musca domestica* (WHO strain) | Housefly | Adult | Plastic pot/Cotton wool and sugar solution | Knockdown | 4 hrs |
| BG | *Blattella germanica* | German cockroach | Nymph | Plastic pot/food pellet | Residual | 3 |
| HV | *Heliothis virescens* | Tobacco budworm | 1st Instar larva | Cotton leaf | Residual | 3 |
| SE | *Spodoptera exigua* | lesser armyworm | 1st Instar larva | Cotton leaf | Residual | 3 |
| DB | *Diabrotica balteata* | Corn rootworm | 3rd Instar larva | Filter paper/ Maize seed | Residual | 3 |

TABLE III

| COMPOUND NO. | EXAMPLE NUMBER | RATE (PPM) | MP | NL | MD/K | MD | BG | HV | SE | DB |
|---|---|---|---|---|---|---|---|---|---|---|
| 112 | 5 | 250 | C | A | A | B | C | C | — | A |
| 141 | 6 | 500 | C | C | — | C | A | C | B | C |
| 75 | 7 | 100 | C | A | A | A | C | C | — | A |
| 76 | 8 | 100 | A | C | A | A | B | A | B | A |
| 38 | 9 | 500 | — | C | A | B | C | C | C | C |
| 1 | 12 | 100 | A | A | A | A | B | A | B | A |
| 27 | 13 | 100 | A | A | A | A | A | A | A | C |
| 4 | 14 | 500 | A | B | A | A | C | A | A | C |
| 238 | 15 | 500 | C | C | C | C | C | C | C | C |
| 400 | 16 | 500 | C | C | C | C | C | C | C | C |

We claim:

1. A compound of formula:

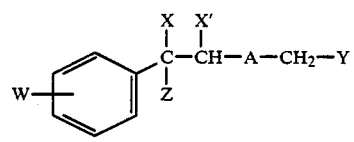

wherein A is a group of formula S(O)$_n$, where n represents 0, 1 or 2; W represents one or two substituents selected from halo, alkyl, alkoxy, alkoxyalkyl, haloalkyl and haloalkoxy, or W represents a bidentate group linking adjacent carbon atoms, selected from alkylene and alkylenedioxy; Y represents a substituted aryl group where each substituent is selected from halo, aryl, aralkyl, aryloxy and arylamino; Z represents a trifluoromethyl group; and either X' is hydrogen and X is selected from hydrogen, halo, hydroxy, alkoxy and acyloxy, or X and X' together represent a second bond between the adjacent carbon atoms.

2. A compound according to claim 1 wherein
W is 4-OC$_2$H$_5$;
X is H;
Z is CF$_3$;
X$^1$ is H;
A is S and
Y is 3-phenoxyphenyl.

3. A compound according to claim 1 of formula IA:

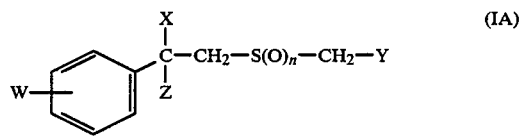
(IA)

wherein W represents one or two substituents selected from halo, alkyl of up to six carbon atoms, alkoxy of up to six carbon atoms, alkoxyalkyl of up to a total of six carbon atoms, haloalkyl of up to six carbon atoms, and haloalkoxy of up to six carbon atoms, or W represents a bidentate group linking adjacent carbon atoms selected from alkylene of up to six carbon atoms and alkylenedioxy of up to a total of six carbon atoms; X is selected from hydrogen, halo, hydroxy, alkoxy of up to six carbon atoms and alkylcarbonyloxy of up to six carbon atoms; Y represents an aryl group selected from phenyl, pyridyl and furyl, substituted with one or more substituents selected from fluoro, methyl, phenyl, benzyl, phenoxy, chlorophenoxy, fluorophenoxy, bromophenoxy and fluoroanilino; Z represents a trifluoromethyl group; and n may have a value selected from 0, 1 and 2.

4. A compound of formula IA as claimed in claim 2 wherein Z represents the trifluoromethyl group; W represents a substituent in the 4-position selected from chloro, methoxy, ethoxy, trifluoromethyl, trifluoromethoxy and difluoromethoxy; Y represents a phenoxyphenyl or a phenoxypyridyl group in which the phenyl or pyridyl rings may be unsubstituted or substituted with halogen; X is selected from hydrogen, fluoro and chloro; and n has the value 0.

5. A process for preparing a compound of formula:

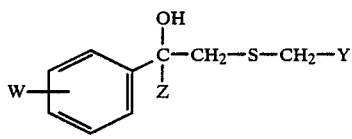

wherein W, Y and Z are as defined in claim 1, which comprises reacting a compound of formula:

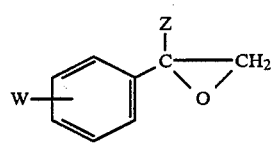

with a compound of formula HS-CH$_2$Y in the presence of a base.

6. A process of preparing a compound of formula:

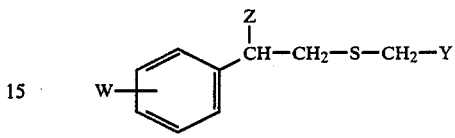

wherein W, Y and Z are as defined in claim 1, which comprises reacting a compound of formula:

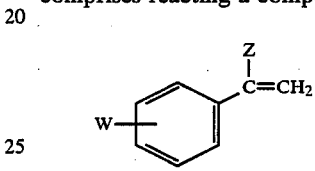

with a compound of formula:

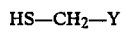

7. A process for preparing a compound of formula:

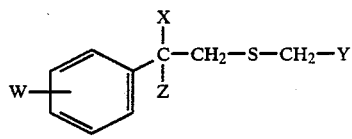

wherein W, Z and Y have any of the meanings given in claim 1 and X represents halo, which comprises reaction of a corresponding compound of formula:

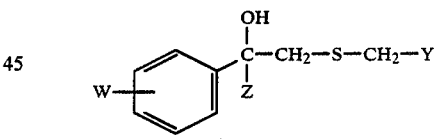

with a halogenating agent.

8. A process for preparing a compound as defined in claim 1, wherein A represents a group of formula S(0)$_n$ and n has a value selected from 1 and 2, which comprises treating a corresponding compound as defined in claim 1, wherein A represents a group of formula S(0)$_n$ and n has the value 0, with an oxidising agent.

9. A process for preparing a compound according to claim 1, wherein A represents a group of formula S(0)$_n$ and n has a value of 1 or 2, which comprises oxidation of a corresponding compound according to claim 1 wherein n is 0.

10. An insecticidal composition comprising an insecticidally effective amount of a compound according to claim 1 in association with an insecticidally inert diluent or carrier.

11. A method of combating insect pests at a locus which comprises applying to the locus an insecticidally effective amount of a composition according to claim 10.

* * * * *